United States Patent [19]

Howells

[11] Patent Number: 4,533,713

[45] Date of Patent: Aug. 6, 1985

[54] FLUOROALIPHATICSULFONAMIDES CONTAINING OXIRANE GROUPS AND/OR N-β-HYDROXYALKYLENE GROUPS

[75] Inventor: Richard D. Howells, P.O. Box 33427, St. Paul, Minn. 55133

[73] Assignee: Minnesota Mining and Manufacturing Company, St. Paul, Minn.

[21] Appl. No.: 492,452

[22] Filed: May 6, 1983

[51] Int. Cl.$^3$ .................... C08G 59/30; C08G 59/28
[52] U.S. Cl. .......................... 528/26; 528/28, 528/70; 528/98; 528/99; 528/363; 528/391; 548/309; 548/310; 549/546; 549/547; 549/551; 549/552; 556/423; 564/82; 564/96; 564/97
[58] Field of Search ............... 549/552, 546, 547, 551; 564/96, 82, 97; 528/391, 363, 26, 28, 70, 98, 99; 548/309, 310; 556/423

[56] References Cited

U.S. PATENT DOCUMENTS

| | | | |
|---|---|---|---|
| 3,255,131 | 6/1966 | Albrecht et al. | 260/22 |
| 3,458,571 | 7/1969 | Tokoli | 260/556 |
| 3,852,222 | 12/1974 | Field et al. | 260/2 |
| 3,879,430 | 4/1975 | O'Rear et al. | 260/348 |
| 4,045,408 | 8/1977 | Griffith et al. | 260/47 |
| 4,132,681 | 1/1979 | Field et al. | 260/836 |
| 4,157,358 | 6/1979 | Field et al. | 260/836 |
| 4,255,299 | 3/1981 | Daimon et al. | 260/17 R |
| 4,265,831 | 5/1981 | Mitschke et al. | 564/96 |
| 4,267,302 | 5/1981 | Ohmori | 528/103 |
| 4,284,746 | 8/1981 | Ohmori | 525/510 |
| 4,284,747 | 8/1981 | Griffith et al. | 525/530 |

FOREIGN PATENT DOCUMENTS 5772977  5/1982  Japan .

OTHER PUBLICATIONS

James R. Griffith, "Epoxy Resins Containing Fluorine", Chemtech, May 1982, pp. 290–293.

Primary Examiner—Earl A. Nielsen

[57] ABSTRACT

Compounds containing (a) a fluoroaliphaticsulfonamido moiety, and (b) a moiety containing (1) at least two oxirane groups, (2) at least two non-terminal N-β-hydroxyalkylene groups, or (3) at least one oxirane group and at least one non-terminal N-β-hydroxyalkylene group. The compound is capable of being cured with a curing agent to give a cured product having excellent water resistance and oil resistance.

17 Claims, No Drawings

FLUOROALIPHATICSULFONAMIDES CONTAINING OXIRANE GROUPS AND/OR N-β-HYDROXYALKYLENE GROUPS

This invention relates to fluoroaliphaticsulfonamides and to epoxy compounds modified by the addition of fluoroaliphaticsulfonamido groups.

Preparation of epoxy resins from polyhydric phenols is well known. An example of such an epoxy resin is the diglycidyl ether formed from Bisphenol A (4,4'-isopropylidenediphenol) and epichlorohydrin(1-chloro-2,3-epoxypropane). Under suitable reaction conditions, this resin can be polymerized, with additional Bisphenol A, to obtain products having molecular weights as high as, or even higher than, 100,000. These polymers have been used in many applications, for example, bulk castings and thin coatings, where their properties, such as chemical resistance, thermal stability, durability, and insulation resistance, are advantageous. However, for some applications, their relatively high surface energy is a detriment. The high surface energy of conventional eepoxy resins makes wetting of low energy, hard-to-wet surfaces difficult without the use of a surfactant and leads to poor leveling during the bake cycle. These shortcomings can lead to inferior coatings, particularly with respect to appearance and corrosion protection. For other applications, the relatively high water absorption of cured epoxy resin systems results in undesirable changes in mechanical and electrical properties.

Among properties characteristic of compounds containing fluorocarbon groups are low surface energy, low oil solubility, low water solubility, low refractive index, low rate of sound transmission, and low dielectric constant. Incorporation of such properties to epoxy compounds would be desirable in order to provide epoxy compounds having improved wetting, flow, solvent resistance, optical, acoustic, and electrical insulation properties.

Property enhancement of conventional epoxy resins has been achieved to some degree through the use of fluorine-containing curing agents to cure the epoxy resins. Epoxy resin curing agents having a pendant perfluoroaliphatic radical have been shown to provide more hydrophobicity and lower surface energy to epoxy resins than curing agents lacking such radicals. Examples of particularly useful fluorine-containing curing agents are represented by the following formulas:

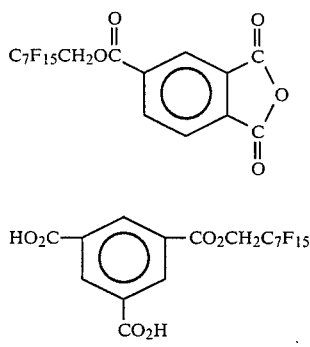

The foregoing curing agents have been shown to render epoxy resin systems hydrophobic. Tokoli, U.S. Pat. No. 3,458,571 discloses perfluoroalkyl-substituted amines used as curing agents for epoxy resins. Examples of these amines are

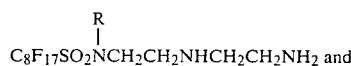

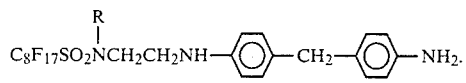

Ohmori, U.S. Pat. No. 4,267,302, discloses an epoxy resin composition which comprises (1) a mono-epoxide having at least one perfluoroalkyl group in one molecule, and (2) an epoxy resin having two or more epoxy groups in one molecule. Upon curing with a curing agent, the composition forms a hardened coating film or hardened molded product, the surface of which is claimed to have excellent water- and oil-repellancy.

Ohmori, U.S. Pat. No. 4,284,746, discloses a curable epoxy resin composition comprising (1) an epoxy resin having at least two epoxy groups per molecule and (2) an amine having at least one perfluoroalkyl group and at least one primary or secondary amino group per molecule. It is claimed that the composition can be cured to afford a cured product having excellent water resistance, oil resistance, and stainproof property.

This invention provides compounds containing
(A) a fluoroaliphaticsulfonamido moiety, and
(B) a moiety containing
 (1) at least two oxirane groups,
 (2) at least two non-terminal N-β-hydroxyalkylene groups, or
 (3) at least one oxirane group and at least one non-terminal N-β-hydroxyalkylene group.

The moiety (A) is linked to the moiety (B) by means of an organic linkage, e.g. —CH$_2$—, or by a covalent bond.

As used in this application, the term "compound" means a chemical substance of particular molecular identity, including a combination or mixture of such substances, whether monomeric, oligomeric, or polymeric in nature.

Classes of compounds within the scope of this invention have the following general formulas.

wherein
R$_f$ represents a monovalent fluoroaliphatic radical,
R$^1$ represents a member selected from the group consisting of

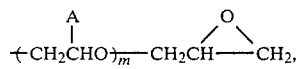

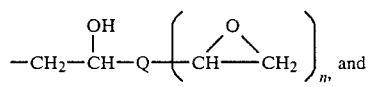

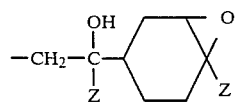

m is an integer equal to or greater than 0,
n is an integer equal to or greater than 1, Q represents a linking group, A represents hydrogen or hydrocarbon radical, such as alkyl having, for example, 1 to 10 carbon atoms, alkenyl having, for example, 1 to 10 carbon atoms, aryl, for example, phenyl, aralkyl, for example, benzyl, alkoxymethyl, for example, butoxymethyl, and aryloxymethyl, for example, phenoxymethyl, and Z represents hydrogen or methyl radical.

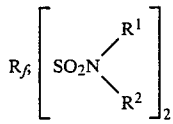    II wherein $R_f'$ represents a divalent fluoroaliphatic radical, $R^1$ is as defined for Formula I, $R^2$ represents a member selected from the group consisting of hydrogen, an unsubstituted hydrocarbon radical, such as alkyl having, for example, 1 to 19 carbons and preferably 1 to 8 carbons, a straight chain alkenyl having, for example, 3 to 18 carbon atoms, aryl such as phenyl, or alkaryl such as benzyl, cycloalkyl having, for example, 5 to 20 carbon atoms, a substituted hydrocarbon radical having a halogen, lower alkoxy, alkoxycarbonyl, or acyloxy substituent group, and $R^1$.

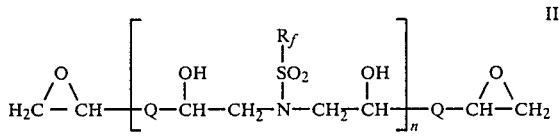    III wherein n is an integer equal to or greater than 1, and $R_f$ and Q are as defined for Formula I.

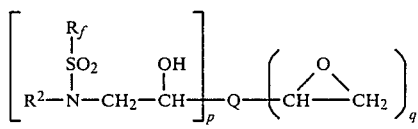    IV wherein p is an integer equal to or greater than 1, q is an integer equal to or greater than 0, p+q is equal to or greater than 2, $R_f$ and Q are as defined for Formula I, and $R^2$ is as defined for Formula II.

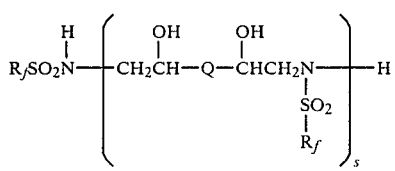    V wherein s is an integer equal to or greater than 1, and $R_f$ and Q are as defined for Formula I.

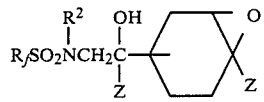    VI wherein $R_f$ and Z are as defined for Formula I, and $R^2$ is as defined for Formula II.

The numbers represented by the letters m, n, p, q and s have an upper practical limit of about 30. Generally, the numbers represented by these letters will range from 1 to 10.

The monovalent fluoroaliphatic radical, $R_f$, is a fluorinated, stable, inert, non-polar, preferably saturated, monovalent moiety which is both oleophobic and hydrophobic. It can be straightt chain, branched chain, and, if sufficiently large, cyclic, or combinations thereof, such as alkylcycloaliphatic radicals. While $R_f$ can have a large number of carbon atoms, compounds where $R_f$ is not more than 20 carbon atoms will be adequate and preferred since large radicals usually represent a less efficient utilization of fluorine than is possible with smaller $R_f$ radicals. The large radicals also are generally less soluble in organic solvents. Generally, $R_f$ will have 1 to 20 carbon atoms, preferably 4 to about 10, and will contain 40 to 83 weight percent, preferably 50 to 78 weight percent, fluorine. The terminal portion of the $R_f$ group preferably has at least three fully fluorinated carbon atoms, e.g. $CF_3CF_2CF_2$—, and the preferred compounds are those in which the $R_f$ group is fully or substantially completely fluorinated, as in the case where $R_f$ is perfluoroalkyl, $C_nF_{2n+1}$, where n is 1 to 20.

The fluoroaliphatic radical, $R_f'$, is a fluorinated, stable, inert, non-polar, preferably saturated, divalent moiety. It can be straight chain, branched chain, and, if sufficiently large, cyclic, or combinations thereof, such as alkylcycloaliphatic diradicals. While $R_f'$ can have a large number of carbon atoms, compounds where $R_f'$ is not more than 20 carbon atoms will be adequate and preferred. Generally, $R_f'$ will have 1 to 10 carbon atoms, preferably 1 to about 6. The preferred compounds are those in which the $R_f'$ group is fully or substantially completely fluorinated, as in the case where $R_f'$ is perfluoroalkyl, $C_nF_{2n}$, or perfluorocycloalkyl, $C_nF_{2n-2}$, where n is 1 to 20.

With respect to either $R_f$ or $R_f'$, the skeletal chain of carbon atoms can be interrupted by divalent oxygen or trivalent nitrogen hetero atoms, each of which is bonded only to carbon atoms, but preferably where such hetero atoms are present, such skeletal chain does not contain more than one said hetero atom for every two carbon atoms. An occasional carbon-bonded hydrogen atom, bromine atom, or chlorine atom may be present; where present, however, they preferably are present not more than once for every two carbon atoms in the chain. Where $R_f$ or $R_f'$ is or contains a cyclic structure, such structure preferably has 5 or 6 ring member atoms, 1 to 2 of which can be said hetero atoms, i.e., oxygen and/or nitrogen. Examples of $A_f$ radicals are fluorinated alkyl, e.g. $C_6F_{13}$—, $C_8F_{17}$—, alkoxyalkyl, e.g. $C_3F_7OCF_2$—. Examples of $R_f'$ are fluorinated alkylene, e.g. —$C_4F_8$—, —$C_6F_{12}$—. Where $R_f$ is designated as a specific radical, e.g. $C_8F_{17}$—, it should be understood that this radical can represent an average structure of a mixture, e.g. $C_6F_{13}-$ to $C_{10}F_{21}-$, which mixure can also include branched structures.

Generally, the compounds of this invention will contain about 5 to about 65 weight percent, preferably about 20 to about 55 weight percent, of carbon-bonded fluorine. Fluorine contents greater than about 65 weight percent are unnecessary to achieve the desired surface properties.

The function of the linking group, Q, is to bond the N-β-hydroxyalkylene sulfonamido group to one, or more, oxirane groups or N-β-hydroxyalkylenesulfonamido groups. Where a compound has more than one such linking group, Q, they can be the same or different. Q can also provide useful properties characteristic of epoxy resins, particularly in formulations where the compounds of this invention comprise the major portion of the formulation. The linking group for a specific compound of this invention will be dictated by the ease of preparation of such a compound and the availability of necessary precursors thereof.

Linking groups can be of three characteristic types: (1) a single distinct residue to which was originally attached two or more oxirane groups, (2) a residue comprising a multiplicity of repeating units to which was originally attached two oxirane groups, and (3) a multiplicity of repeating residues to which was attached skeletal or pendant oxirane groups. The term "residue", when used to refer to a compound, means the portion of the compound which is separate or devoid of the oxirane groups.

Examples of the first type of linking group Q are:

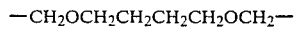

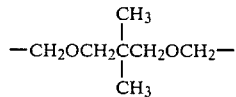

$CH_3CH_2C(CH_2OCH_2-)_3$

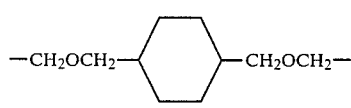

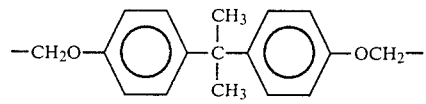

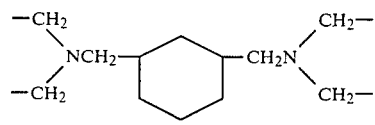

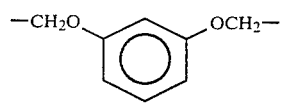

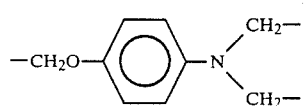

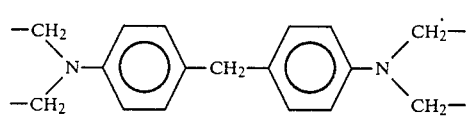

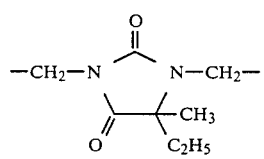

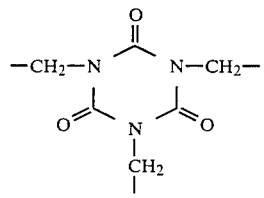

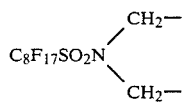

Examples of the second type of linking group Q are:

$-(CH_2)_4-$

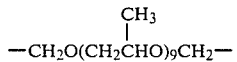

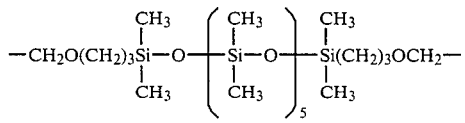

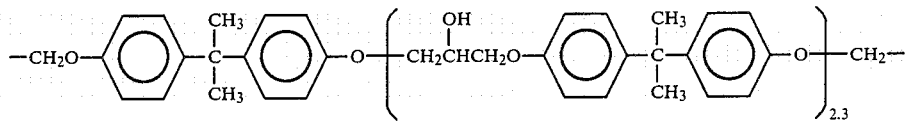

Examples of the third type of linking group Q are:

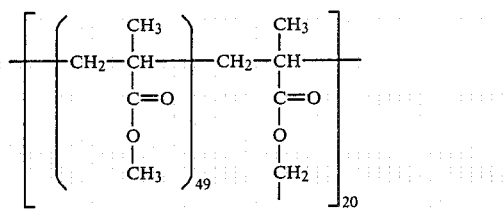

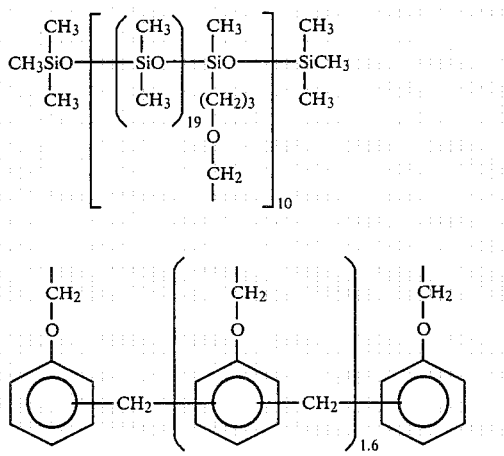

From the above description of the linking groups, it is apparent that these linkages can have a wide variety of structures. For example, Q can be an alkylene group, an aralkylene group, a poly(oxyalkylene) group, an arylene group, a carbonyl group, a sulfonyl group and various combinations of these groups. Such groups can also include other hetero moieties, besides —O—, such as, for example $$-\overset{|}{\underset{|}{Si}}-,\ -\overset{|}{N}-,$$

and —S—. In addition, Q can be a covalent bond. Q can also be substituted with such substituents as halogen atoms and fluoroaliphatic radicals. However large the linking group is, the fluorine content (the locus of which is $R_f$ or $R_f'$) of the compounds of this invention is within the aforementioned limits.

Epoxy-containing materials useful for preparing the compounds of this invention must either possess more than one oxirane ring, i.e.

$$-\overset{|}{\underset{\diagdown O \diagup}{C}}\overset{|}{\underset{}{C}}-$$

or a single oxirane ring vicinal to a group capable of being displaced, i.e.

$$-\overset{|}{\underset{\diagdown O \diagup}{C}}\overset{|}{\underset{}{C}}-\overset{|}{\underset{|}{C}}-X$$

wherein X represents a displaceable group.

The preferred displaceable groups are chlorine or bromine.

Such epoxy-containing starting materials, broadly called epoxides, include monomeric epoxy compounds and epoxides of the polymeric type and can be aliphatic, cycloaliphatic, aromatic, or heterocyclic. The polymeric epoxides include linear polymers having terminal epoxy groups (e.g., a diglycidyl ether of a polyoxyalkylene glycol), polymers having skeletal oxirane units (e.g. polybutadiene polyepoxide), and polymers having pendant epoxy groups (e.g., a glycidyl methacrylate polymer or copolymer). The molecular weight of the epoxy-containing materials can vary from 93 to about 100,000 or more. Mixtures of various epoxy-containing materials can also be used in the compositions of this invention.

Epoxy-containing materials useful for preparing the compounds of this invention include epichlorohydrin and those which contain at least one aliphatic alkene oxide group such as 1,6-hexadiene oxide and vinylcyclohexene dioxide.

Further epoxy-containing materials which are particularly useful for preparing the compounds of this invention include glycidyl ether or glycidyl amine monomers of the formula $$R + Y-CH_2-CH \underset{\diagdown O \diagup}{\qquad} CH_2)_t$$

where R represents an alkyl or aryl group, Y is oxygen or nitrogen, or a combination thereof, and t is greater than one, preferably 2 to 8. Representative examples are the glycidyl derivatives of polyhydric alcohols, phenols, aromatic amines, or amino phenols obtained by reacting said polyhydric, active hydrogen-containing compounds (e.g., pentaerythritol, resorcinol, aniline, and p-aminophenol) with epichlorohydrin. Further examples of epoxides of this type which can be used in the practice of this invention are described in U.S. Pat. No. 3,018,262, incorporated herein by reference, in "Handbook of Epoxy Resins" by Lee and Neville, McGraw-Hill Book Co., New York (1967), in "Epoxy Resin Technology" by P. F. Bruins, John, Wiley & Sons, Inc., New York (1968), and in "Handbook of Composites" by G. Lubin, Van Nostrand Reinhold Co., New York (1982).

There is a host of commercially available epoxy-containing materials which can be used to prepare the compounds of this invention. In particular, epoxides which are readily available include 1,4-butanediol diglycidyl ether (e.g., "Araldite RD-2" from Ciba-Geigy), neopentyl glycol diglycidyl ether (e.g., "Heloxy 68" from Wilmingtom Chemical Company), cyclohexanedimethanol diglycidyl ether (e.g., "Heloxy MK-107" from Wilmingtom Chemical Company), polyoxypropylene glycol diglycidyl ether (e.g., "DER-736" and "DER-732" from Dow Chemical Company), hydrogenated Bisphenol-A diglycidyl ether (e.g., "Eponex 1510" from Shell Chemical Company), 1,3-bis(3-glycidoxypropyl)tetramethyldisiloxane (e.g., "B-2405" from Petrarch Systems), trimethylolpropane triglycidyl ether (e.g., "Epi-Rez 5048" from Celanese Coatings and Specialties), diglycidyl 1,2-cyclohexanedicarboxylate (e.g., "Araldite CY-183" from Ciba-Geigy), Bisphenol-A diglycidyl ether (e.g., "Epon 828", "Epon 836", and "Epon 1001" from Shell Chemical Company, "DER-332" from Dow Chemical Company, and "Araldite 6060" from Ciba-Geigy), phenolformaldehyde novolac polyglycidyl ether (e.g., "DEN-438" from Dow Chemical Company and "LSU-938" from Ciba-Geigy), methylenedianiline tetraglycidyl amine (e.g., "XU-235" from Ciba-Geigy), 1,3-di(aminomethyl)cyclohexane tetraglycidyl amine (e.g., "PGAC" from Sherwin-Williams), 5-ethyl-5-methyl-1,3-diglycidylhydantoin (e.g., "XU-238" from Ciga-Geigy), triglycidyl isocyanurate (e.g., "Araldite PT-810" from Ciga-Geigy), and mixtures thereof.

Representative $R_f$ intermediates for the preparation of the compounds of this invention include:

$$C_8F_{17}SO_2\overset{H}{N}C_2H_5$$

$$C_8F_{17}SO_2NH_2$$

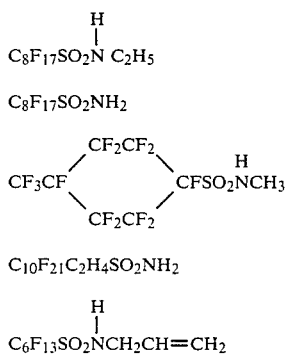

$$C_{10}F_{21}C_2H_4SO_2NH_2$$

$$C_6F_{13}SO_2\overset{H}{N}CH_2CH=CH_2$$

Representative $R_f'$ intermediates for the preparation of the compounds of this invention include:

$$H_2NO_2S(CF_2)_4SO_2NH_2$$

$$CH_3\overset{H}{N}O_2S(CF_2)_4SO_2\overset{H}{N}CH_3$$

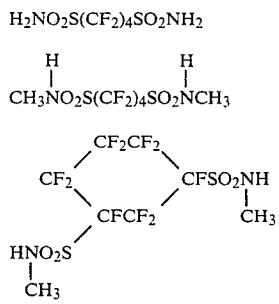

Compounds of this invention represented by the formula

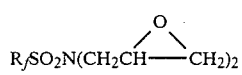

can be prepared by reacting a difunctional fluoroalkanesulfonamide with a stoichiometric amount of epichlorohydrin or an excess of epichlorohydrin in the presence of a base. Although the active hydrogen equivalent ratio of the fluoroalkanesulfonamide to the epichlorohydrin can be as low as 1:1, the preferred active hydrogen equivalent ratio is about 1:10 to about 1:12. However, the ratio can be higher.

Bases that are suitable for conducting the reaction include alkali metal hydroxides, e.g. sodium hydroxide and potassium hydroxide, and tertiary amines, e.g. triethylamine.

The base is preferably added to the reaction mixture in incremental amounts or in a slow continuous fashion. Generally, from about 0.1 to about 0.2 equivalent of base per equivalent of active hydrogen in the fluoroalkanesulfonamide is sufficient for the initial stage of the reaction, wherein chlorohydrin intermediates are formed (see Scheme 1 below).

In order to initiate the reaction, it is preferable to elevate the temperature of the reaction mixture to about 65° C. to about 75° C. Because the initial stage of the reaction is exothermic, the temperature thereof is preferably maintained within that range by removal of the heating source, or by cooling, as required. The remainder of the stiochiometric amount of base is then added in incremental amounts or continuously.

The product can then be recovered by water washing or filtration, to remove salt by-products, followed by distillation to remove excess epichlorohydrin.

The remaining compounds represented by formulas I, II, III, IV, V, and VI, those which contain the N-β-hydroxyalkylene group can be prepared by reacting a fluoroaliphaticsulfonamide with a compound having at least two oxirane groups at elevated temperatures in the presence of a catalyst, e.g. tertiary amines, quarternary ammonium halides, phosphonium halides, and metal hydrides.

The concentration of catalyst is preferably about 0.02 to about 0.5 percent by weight, based on the weight of total solids. The reaction is generally conducted at a temperature ranging from about 90° C. to about 180° C.

Representative reaction schemes for the preparation of the compounds of this invention are outlined below, where the products designated in the manner I', II', III', IV', V', VI' are species of Formula I, Formula II, Formula III, Formula IV, Formula V, and Formula VI respectively.

SCHEME 1

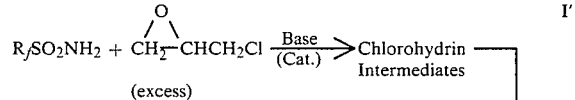

SCHEME 2

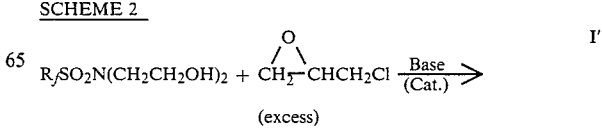

-continued

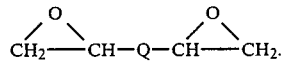
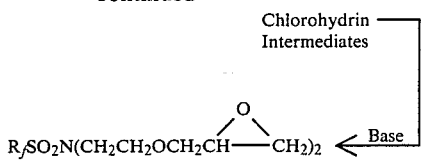

SCHEME 3

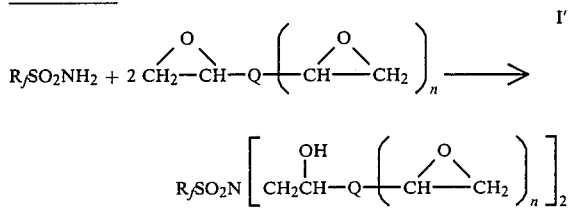

SCHEME 4

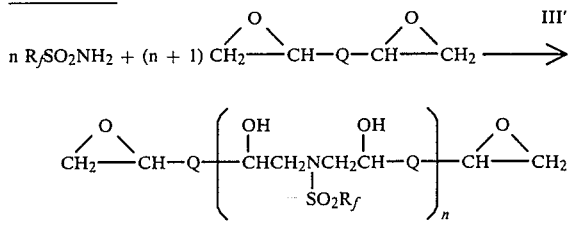

SCHEME 5

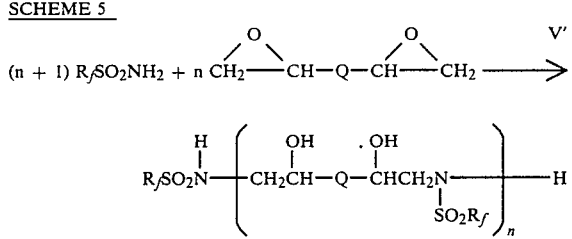

SCHEME 6

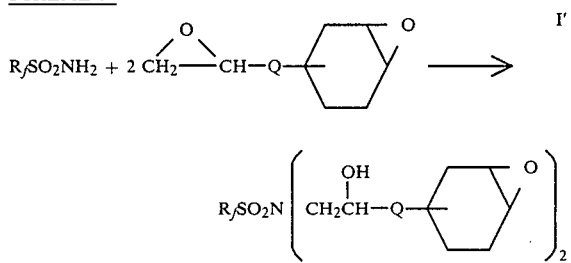

SCHEME 7

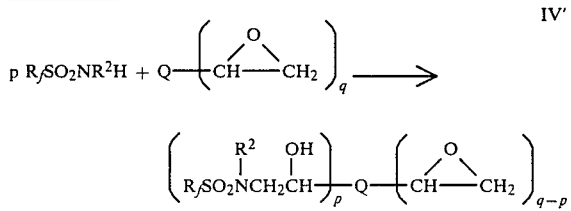

SCHEME 8

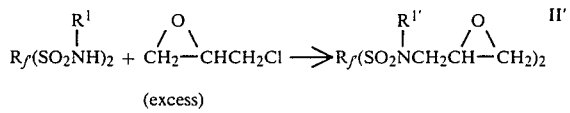

(excess)

wherein $R^1$ need not be the same as $R^{1'}$.

Although the reaction conditions for preparing compounds represented by Formulas I, II, III, IV, V, and VI are similar, the particular products formed are influenced by the relative amounts of each reactant. For example, it is apparent from Reaction Schemes 4 and 5 that the reaction products formed depend upon the molar ratio of the reactant $R_fSO_2NH_2$ to the reactant $$CH_2\overset{O}{-\!\!\!-\!\!\!-}CH-Q-CH\overset{O}{-\!\!\!-\!\!\!-}CH_2.$$

The fluoroaliphaticsulfonamido epoxy compounds and resin compositions of the present invention can be cured according to known methods for curing conventional epoxy resins. For example, the epoxy resin can be cured by adding a curing agent such as a polyamine, e.g. a diamine, and reacting at 25° C. followed with heating to about 100° C. or higher. Other classes of curing agents that are suitable for curing the compounds of the present invention include anhydrides, polycarboxylic acids, and diisocyanates. The amount of curing agent can vary in accord with well-established principles of conventional epoxy resin cure chemistry. In addition, curing agents containing fluorocarbons can be used to cure the compounds of this invention. The use of such curing agents will result in cured compositions having high fluorine content. The compounds of this invention can be blended with conventional epoxy resins and other co-reactants such as polyols to form curable compositions.

Optionally, the curable composition can contain other additives, for example, fillers, pigments, antioxidants, reinforcing fibers, and the like.

The cured compounds of the present invention have improved water-resistant, oil-resistant and stain resistant properties when compared with conventional cured epoxy resins. The cured products of this invention can be used as coating films, laminates, insulating materials, castings, and adhesives.

The oleophobicity and hydrophobicity of coatings prepared from the compounds of this invention makes these coatings particularly useful in the areas of protective coatings for pipes used to transport oil or water, marine coatings, fouling release coatings, container coatings, automobile coatings, and underwater composites.

The compounds of the present invention are also useful for preparing acoustically-transparent plastics for underwater applications.

The compounds of the present invention can also be used to prepare polyurethanes, polyacrylates, and other polyesters.

The following examples, which are illustrative rather than limiting or delineative of the scope of the invention, serve to describe the novel compounds, their method of preparation, and their properties.

EXAMPLE I

Preparation of N,N-Bis(2,3-epoxypropyl)perfluorooctanesulfonamide

Into a 500 mL three-necked flask equipped with a thermometer, an agitator, and reflux condenser were charged 225 g (2.43 moles) of epichlorohydrin and 100 g (0.21 mole) of perfluorooctanesulfonamide. The mixture was stirred and heated to 50° C., and 1 g (0.025 mole) of granular sodium hydroxide and 1.1 g (0.011 mole) of triethylamine were then added. The reaction mixture was then heated to 65° C. and maintained at that temperature for 3½ hours. Chromatographic analysis indicated that the reaction product contained 64.8% N,N-bis(3-chloro-2-hydroxypropyl)perfluorooctanesulfonamide, 1.6% N-(3-chloro-2-hydroxypropyl)perfluorooctanesulfonamide, and 33.3% N-(2,3-epoxypropyl)-N-(3-chloro-2-hydroxypropyl)perfluorooctanesulfonamide.

By means of a syringe pump, 40 g (0.50 mole) of 50% aqueous sodium hydroxide was added to the reaction mixture over a period of 4.5 hours, during which time the mixture was stirred and maintained at 65°–70° C. At the end of the addition, chromatographic analysis indicated that the reaction product contained 86.1% N,N-bis(2,3-epoxypropyl)perfluoroctanesulfonamide and 6.2% of N-(3-chloro-2-hydroxypropyl)perfluorooctanesulfonamide.

The reaction mixture was cooled to 40° C. and washed with three 100 ml portions of distilled water to remove sodium chloride. The excess epichlorohydrin was then removed by vacuum distillation. The distillation was started at approximately 60° C. and 100 torr and taken to 100° C. and 20 torr, where it was held for one hour.

The product yield was 117 g (95% of theory). Chromatographic analysis indicated that the reaction product contained 88.0% N,N-bis(2,3-epoxypropyl)perfluroctanesulfonamide, 5.2% N-(3-chloro-2-hydroxypropyl)perfluorooctanesulfonamide. The remainder comprised several unidentified components. The product had an epoxy equivalent weight (EEW) of 335 (theoretical, 306).

EXAMPLE II

Preparation of
N,N-Bis(2,3-epoxypropyl)perfluorooctanesulfonamide

To a 3 neck, 2 L reaction flask equipped with an agitator, reflux condenser, and thermometer was placed 925 g (10 moles) of epichlorohydrin, and 484 g (1 mole) of perfluorooctanesulfonamide. The mixture was stirred and heated to 50° C., and then 8 g (0.2 mole) of sodium hydroxide pellets and one drop of water were added. The reaction mixture was stirred and heated to 65° C., at which temperature a mild exotherm was observed. The temperature was maintained at 65°–75° C. for two hours. A second addition of 8 g of sodium hydroxide pellets was made and the stirred reaction mixture was heated at 65°–75° C. for one hour. A gas chromatographic (GC) analysis of a small sample of the reaction mixture indicated the presence of the intermediate N,N-bis(3-chloro-2-hydroxypropyl)perfluorooctanesulfonamide as the major perfluorooctanesulfonamide derivative present. To convert the foregoing intermediate to the desired diepoxide, 64 g (1.6 moles) of sodium hydroxide pellets were added in 8 g increments at one-half hour intervals to the stirred, heated (60° C.) reaction mixture. After the last addition, the mixture was heated for a period of one hour at 60° C. GC analysis of a small sample of the reaction mixture showed a 78.5% conversion to N,N-bis(2,3-epoxypropyl)perfluoroctanesulfonamide. The reaction mixture was filtered to remove sodium chloride and the excess epichlorohydrin removed under vacuum at 60°–75° C. pot temperature. The crude diepoxide product thus isolated had an EEW of 378.

EXAMPLE III

Preparation of
N,N-Bis(2,3-epoxypropyl)perfluorohexanesulfonamide

The procedure of Example II was repeated, the only exception being that perfluorohexanesulfonamide was used in place of perfluorooctanesulfonamide, to prepare the diepoxide product. The crude product had a EEW of 314, and a distilled sample (boiling range, about 120°–130° C. at 0.1 torr) had a EEW of 284 (theoretical, 256).

EXAMPLE IV

Preparation of
N,N-Bis(2-glycidoxyethyl)perfluorooctanesulfonamide

Into a 1 L 3-neck flask equipped with an agitator, thermometer, and a reflux condenser was placed 171 g (0.3 mole) of N,N-bis(2-hydroxyethyl)perfluorooctanesulfonamide (prepared from perfluorooctanesulfonamide and ethylenechlorohydrin as described in Example 2 of U.S. Pat. No. 4,289,892) and 277.5 g (3.0 moles) of epichlorohydrin. The reaction mixture was stirred and heated to 65° C. Then 12.2 g (of a total of 53 g, 1.3 moles) of sodium hydroxide was added. The reaction mixture was heated to 90° C. and stirred at that temperature for 4 hours, cooled to about 40° C., and filtered from sodium chloride. The filter cake was then washed with about 50 mL epichlorohydrin. The combined filtrates along with the remaining sodium hydroxide were heated to 90° C. and stirred at that temperature for 4 hours. The reaction mixture was cooled, filtered, and the filtrate concentrated under vacuum at a temperature of 50° to 90° C. to remove excess epichlorohydrin. GC and infrared spectroscopic (IR) analysis of the product indicated the presence of N,N-bis(2-glycidoxyethyl)perfluorooctanesulfonamide in about 90% purity. The impurity was mainly N-(2-hydroxyethyl), N(2-glycidoxyethyl)perfluorooctanesulfonamide.

EXAMPLE V

Preparation of
N,N'-Dimethyl-N,N'-bis(2,3-epoxypropyl)octafluorobutane-1,4-disulfonamide Into a 500 mL flask fitted with agitator, reflux condenser, thermometer and heating mantle was placed 77.6 g (0.2 mole) of N,N'-dimethyloctafluorobutane-1,4-disulfonamide (prepared from octafluorobutane-1,4-disulfonyl fluoride and methylamine) and 129.5 g (1.4 moles) of epichlorohydrin. The reaction mixture was stirred and heated to 60°–65° C. To the reaction mixture was added 1.5 g (of a total of 17.2 g, 0.42 mole) of sodium hydroxide pellets and 2 drops of water. The remaining sodium hydroxide was added in portions over about a one hour period at a rate sufficient to maintain the pot temperature at approximately 65° C. without external heating. The exothermic reaction provided the required heat. After the addition of sodium hydroxide was complete, the reaction mixture was cooled to about 40° C., filtered to remove sodium chloride, and stripped of the excess epichlorohydrin under reduced pressure. The yield of crude diepoxide product, m.p. 75°–80° C., was 101 g (theoretical, 100 g). GC analysis indicated a purity of 93% for the desired diepoxide compound. Recrystallization from ethyl alcohol gave product melting at 77°–79° C. having 96% purity, as determined by GC. The structure of the diepoxide product was supported by proton nuclear magnetic resonance (NMR) analysis and IR analysis.

EXAMPLE VI

This example describes the polymerization of the diepoxide product from Example I employing various curing agents. The curing agents (listed in Table 1) were mixed in the indicated amounts (Table 2) with the diepoxide product, and 2 to 3 g of each liquid mixture were placed in a 5 cm diameter aluminum pan and cured in an oven under the conditions shown in Table 2. All compositions cured to hard solids having surface energies as indicated. The surface energies were calculated from contact angle measurements using drops of $CH_2I_2$ and glycerine placed on the surface of the solid castings, employing the procedure described by D. K. Owens et al. in the Journal of Applied Polymer Science, 13, 1741–1747 (1969). As the data in Table 2 show, the surface energies of the cured epoxy compound are low, 16.0 dynes/cm$^2$ or lower.

TABLE 1

| | Curing Agent |
|---|---|
| Code | Name |
| A | Boron trifluoride - ethylamine complex |
| B | Diethylenetriamine |
| C | 2,4,6-tris(dimethylaminomethyl)phenol, ("Capcure EH 30") |
| D | Methyl cyclopentadiene/maleic anhydride adduct ("Kayahard MCD") |
| E | N,N—Dimethylbenzylamine |
| F | Polyoxypropylene diamine ("Jeffamine D-230") |
| G | Bis(5-aminopentyl)tetramethyldisiloxane |

TABLE 2

| Run no. | Amount of epoxy compound[1] (g) | Curing agent[2] | Amount of curing agent (g) | Cure condition[3] | Hardness (Shore D) | Surface energy (dynes/cm$^2$) |
|---|---|---|---|---|---|---|
| 1 | 5.0 | A | 0.21 | a | too brittle to test | 13.8 |
| 2 | 5.15 | B | 0.33 | b | 80 | 13.1 |
| 3 | 5.14 | C | 0.26 | c | too brittle to test | 11.5 |
| 4 | 10.0 | D | 3.03 | a | 83 | 16.0 |
| | | E | 0.13 | | | |
| 5 | 5.17 | F | 0.99 | c | 79 | 12.9 |
| 6 | 4.96 | G | 1.24 | c | 77 | 11.7 |

[1] The epoxy compound was $C_8F_{17}SO_2N(CH_2CH\overset{O}{\overset{\diagup\diagdown}{\phantom{x}}}CH_2)_2$.
[2] The curing agents are set forth in Table 1.
[3] Cure conditions were as follows:
a: 4 hours at 100° C. and 16 hours at 150° C.
b: 4 hours at 20° C. and 3 hours at 100° C.
c: 1 hour at 65° C. and 23 hours at 100° C.

EXAMPLE VII

This example describes the cocuring of various amounts of the diepoxide product of Example I with "ERL-4221" epoxy resin available from Union Carbide Corporation utilizing 0.15 percent by weight of ultraviolet radiation-activated complex salt catalyst, $Ar_3SSbF_6$, as a 50% solution in $CHCl_3$. Castings of 3 g of each composition shown in Table 3 were poured into 5 cm diameter aluminum pans and each casting irradiated several minutes under a 275 watt sun lamp/3 mm quartz glass plate assembly at about 8 cm distance to cause gelation, while a stream of nitrogen was passed over the sample. Curing was completed by heating each casting for 6.5 hours at 100° C. to yield glossy, pale yellow solids. Properties of the cured compositions are shown in Table 3. Surface energy decreased with increasing proportions of the diepoxide product of Example I.

TABLE 3

| Run No. | Amount of ERL-4221 epoxy resin (g) | Amount of diepoxide product of Example I (g) | | Hardness (Shore D) | Water absorption[a] (wt %) | Surface energy (dynes/cm$^2$) |
|---|---|---|---|---|---|---|
| | | (g) | (wt %) | | | |
| 1 | 10.00 | 0 | 0 | 91 | 0.85 | 46 |
| 2 | 10.01 | 0.0124 | 0.12 | 88 | 0.79 | 48 |
| 3 | 9.96 | 0.0618 | 0.62 | 90 | 0.89 | 40 |
| 4 | 9.77 | 0.28 | 2.8 | 88 | 0.93 | 34 |
| 5 | 9.00 | 1.00 | 10.0 | 87 | 0.83 | 27 |
| 6 | 7.51 | 2.48 | 24.8 | 87 | 0.74 | 24 |
| 7 | 5.00 | 5.07 | 50.3 | 87 | 0.50 | 18 |

[a] The sample was immersed for 24 hours at room temperature, and excess water absorbed by towel prior to measurement.

From Table 3 it can be seen that by varying the proportion of the fluorochemical diepoxide product of Example I in a blend containing a conventional epoxy resin, the surface energy of the resulting cured resin can be controlled.

EXAMPLE VIII

This example compares the water absorption of Sample A, a cured epoxy resin composition utilizing the diepoxide product of Example I, with Sample B, a cured epoxy resin composition containing no fluorochemical constituent. Curing was carried out under conditions similar to those described in Example VII using 0.15 weight percent $Ar_3SSbF_6$ catalyst, based on total weight of reactants. The ingredients and amounts thereof for Samples A and B are set forth in Table 4.

TABLE 4

| Ingredient | Amount (percent by weight) | |
|---|---|---|
| | A | B |
| $C_8F_{17}SO_2N(CH_2CH\overset{O}{\overset{\diagup\diagdown}{\phantom{x}}}CH_2)_2$ (from Example I) | 40 | 0 |
| "Epon 828" epoxy resin | 30 | 38.7 |
| "Araldite RD-2" epoxy resin | 0 | 22.7 |
| Phenyl glycidyl ether | 30 | 38.6 |

The cured samples were immersed in water at room temperature for 24 hours and excess water absorbed by paper towel prior to measurement. Sample A absorbed 0.11 percent water (based on total weight of cured epoxy composition) and Sample B absorbed 0.25 percent water. The fluorine-containing cured epoxy resin composition absorbed less than half as much water as the fluorine-free epoxy resin composition.

EXAMPLE IX

In this example, and those following, the preparation or curing of novel perfluorooctanesulfonamide/diepoxide adducts of this invention are described.

Into a 100 mL flask were placed 6.9 g (0.0138 mole) perfluorooctanesulfonamide, 10.0 g (0.276 mole) of bis((b 3-glycidoxypropyl)tetramethyldisiloxane, and (b 0.08 g N,N-dimethylbenzylamine catalyst. The reaction mixture was stirred and heated in an oil bath to 120° C. at which temperature it was maintained for 1.25 hours. The reaction product was a clear orange liquid, comprising mainly a compound represented by the formula

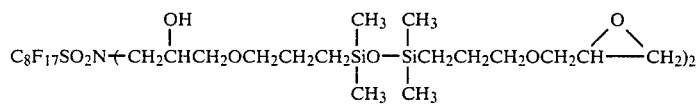

as determined by Ir and NMR analysis. The EEW was found to be 641 (theoretical, 612).

EXAMPLE X

The procedure of Example IX was repeated, the only exception being that "DER-736" epoxy resin was employed. The reaction product was a red-orange liquid comprising mainly a compound represented by the formula

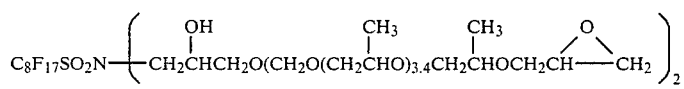

The EEW was found to be 671 (theoretical 640).

EXAMPLE XI

The procedure of Example IX was repeated, the only exceptions being that heating was conducted at 120° C. for 40 minutes, and "XU-238" epoxy resin was employed instead of bis(3-glycidoxypropyl)tetramethyldisiloxane. The reaction product was an orange, glassy solid comprising mainly a compound represented by the formula

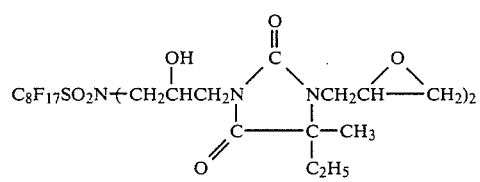

The product was a viscous liquid at 100° C. The EEW was found to be 546 (theoretical, 534).

EXAMPLE XII

The procedure of Example IX was repeated, the only exceptions being that heating was conducted at 100° C. for 4 hours, and "Epon 828" epoxy resin was employed instead of bis(3-glycidoxypropyl)tetramethyldisiloxane. The reaction product was an orange, glassy solid comprising mainly a compound represented by the formula

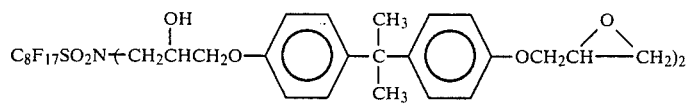

The EEW was found to be 637 (theoretical, 628).

EXAMPLE XIII

In this example, (a) fluorochemical diepoxides of this invention, (b) blends of fluorochemical diepoxides of this invention with epoxy resins not containing fluorine, and (c) epoxy resins not containing fluorine were cured and surface energies of the cured resins measured. The curing agent, methyl cyclopentadiene/maleic anhydride adduct ("Kayahard MCD"), was present in a ratio of 0.6 equivalent per 1.0 equivalent of resin. One percent by weight N,N-dimethylbenzylamine catalyst, based on the weight of the total composition, was also employed.

Each mixture of resin, curing agent, and catalyst was stirred and heated at 100° C. for several minutes to obtain a homogeneous solution. Two grams of each mixture were poured into a 5 cm diameter aluminum pan and cured by heating for 4 hours at 100° C. and then for 16 hours at 150° C. The results are shown in Table 5.

TABLE 5

| Run | Cured resin | Surface energy (dynes/cm$^2$) |
| --- | --- | --- |
| 1 | Diepoxide product of Example XI | 24 |
| 2 | Diepoxide product of Example XII | 23 |
| 3 | 9 parts (wt) diepoxide product of Example X: 10 parts (wt) "Epon 828" epoxy resin | 31 |
| 4 | 11 parts (wt) diepoxide product of Example IX: 13 parts (wt) "Epon 828" epoxy resin | 26 |
| 5 | "Epon 828" epoxy resin | 36 |
| 6 | "XU-238" epoxy resin | 37 |

As Table 5 shows, the cured diepoxide products of this invention and blends thereof provided lower surface energy values than did cured fluorine-free epoxy resins.

EXAMPLE XIV

This example describes the preparation of a fluorochemical oligomeric diepoxide product from perfluorooctanesulfonamide and "Epon 828" epoxy resin. Into a 1 L resin flask equipped with stirrer, thermometer, heating mantle and vacuum line was placed 271 g (1.43 moles) of "Epon 828" epoxy resin. The flask was heated to 70° C. and the pressure reduced to 30 torr. The pressure was brought to atmospheric with nitrogen gas and a 1 L per minute nitrogen gas flow as established. Then, 228 g (0.46 mole) of perfluorooctanesulfonamide and 0.4 g of triphenylethylphosphonium iodide catalyst were added. The reaction mixture was stirred and heated slowly to 180° C. over a two hour period and was then maintained at 180° C. for two additional hours. The product was then poured into aluminum trays to cool. The solid fluorochemical oligomeric diepoxide product had an EEW of 1054, which is consistent for the structure

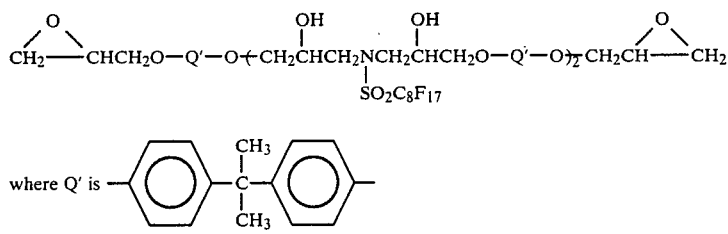

EXAMPLE XV

This example describes the preparation of, and presents the surface energy properties of, blends of the oligmeric diepoxide product of Example XIV with "Epon 1004" epoxy resin (EEW about 900).

The blends were prepared by mixing and melting together in an aluminum dish on a hot plate, 10 g combined weight of the two solid components in the ratios indicated in Table 6. A portion of each liquid blend was coated while hot (about 150° C.) on a glass slide using a wood spatula, yielding a coating which appeared smooth to the unaided eye. The surface energy of each coating was determined by the procedure described in Example VI. The surface energy values are shown in Table 6. As little as 10 percent by weight of the diepoxide product of Example XIV in the blend gives low surface energy (see Run 2).

TABLE 6

| Run No. | Blend component (percent by weight) | | Surface energy (dynes/cm$^2$) |
|---|---|---|---|
| | Diepoxide product of Example XIV | EPON 1004 epoxy resin | |
| 1 | 0 | 100 | 47.7 |
| 2 | 10 | 90 | 19.6 |
| 3 | 20 | 80 | 20.0 |
| 4 | 30 | 70 | 18.7 |
| 5 | 40 | 60 | 20.4 |
| 6 | 50 | 50 | 20.5 |
| 7 | 100 | 0 | 21.8 |

EXAMPLE XVI

This example describes the preparation of a fluorocarbon-modified epoxy resin containing, in addition to epoxy groups, several N-β-hydroxyalkylene fluoroalkanesulfonamido groups in each resin molecule.

Into a 250 mL flask, equipped with agitator, condenser, thermometer and heating mantle, was placed 16.5 g (0.093 equiv.) of "DEN-485" epoxy novolac resin having an EEW of 178 and an epoxy functionality of 5.5. N-Ethylperfluorooctanesulfonamide (37.9 g, 0.0715 equiv.), 30 mL of methyl isobutyl ketone and 5 drops of triethylamine were added to the flask and the mixture stirred and heated for 16 hours at 110° C. The solvent was then removed by distillation and heating was continued for 4 hours at 150° C. The product was a homogeneous, brittle solid with EEW of 2100.

EXAMPLE XVII

This example describes the preparation of a stearic acid-modified, fluorocarbon-modified epoxy resin.

Into a 250 mL flask equipped as described in Example XVI, was placed 16.5 g (0.194 equiv.) "DEN-438" epoxy novolac resin having an EEW of 175 and an epoxy functionality of 3.3, 5.75 g (0.020 equiv.) stearic acid, and 0.05 g of triphenylethylphosphonium iodide. The mixture was stirred and heated to 150° C. to yield a homogeneous solution. Titration of a small sample of the reaction mixture with ethanolic potassium hydroxide indicated complete reaction of stearic acid. To the reaction mixture was then added 37.9 g (0.0715 equiv.) of N-ethylperfluorooctanesulfonamide, and the reaction mixture was stirred and heated for 2 hours at 150° C. The solid epoxy reaction product had an EEW of 5600.

EXAMPLE XVIII

This example describes the reaction of an N-alkylperfluoroalkanesulfonamide and a trifunctional epoxy resin. Into a 250 mL flask equipped as described in Example XVI was placed 159 g (0.30 equiv.) of N-ethylperfluorooctanesulfonamide and 83 g (0.78 equiv.) of N,N,O-triglycidyl-p-aminophenol. The reaction mixture was stirred and heated for 6 hours at 100° C. The product of the reaction was an amber, brittle, glassy diepoxide having an EEW of 503.

EXAMPLE XIX

This example demonstrates an epoxy resin composition having low water absorption. "Eponex 1510" epoxy resin (EEW 235) was reacted with several perfluoroalkanesulfonamido reagents, in stoichiometric amounts, to yield crosslinked solid, glassy products. When two sulfonamido reagents were used, each was present at a concentration of 0.5 equivalent per epoxy equivalent.

A total of 10 g of each reaction mixture was prepared using the amounts of reactants indicated in Table 7, and employing 0.5% by weight of N,N-dimethylbenzylamine catalyst. Each of the reaction mixtures was placed in a 5 cm diameter aluminum pan, and cured for 1 hour at 100° C.

As can be seen from Table 7, the level of water absorption for all runs was low, below 0.20 percent by weight for each run.

TABLE 7

| Run no. | Blend Component (percent by weight) | | | Water absorption, (wt %, 24 hours) |
|---|---|---|---|---|
| | "Eponex 1510" epoxy resin | Fluoroalkanesulfonamide | | |
| | | Code[1] | | |
| 1 | 48.6 | a | 51.4 | 0.15 |
| 2 | 54.1 | b | 45.9 | 0.18 |
| 3 | 58.1 | a | 30.8 | 0.16 |
| | | c | 11.1 | |
| 4 | 61.2 | d | 38.8 | 0.17 |
| 5 | 72.3 | c | 27.7 | 0.15 |
| 6 | 76.1 | e | 23.9 | 0.17 |

[1]The fluoroalkanesulfonamides are represented by the following symbols:
a: Perfluorooctanesulfonamide
b: Perfluorohexanesulfonamide
c: Octafluorobutane-1,4-disulfonamide
d: Perfluorobutanesulfonamide
e: Trifluoromethanesulfonamide

EXAMPLE XX

In this example, an >NH terminated prepolymer (A) was prepared from a 2/1 equivalent ratio of trifluoromethanesulfonamide (FMSA) and "Eponex 1510" epoxy resin, then reacted with another equivalent of "Eponex 1510" epoxy resin to yield the same chain-extended, glassy resin of Example XIX, run 6, in which stoichiometric equivalent amounts of the reagents were reacted in the initial reaction. In this example, the reaction was conducted as follows:

Into a glass vial, were placed 3.8 g "Eponex 1510" epoxy resin, 2.4 g of FMSA, and 1 drop of N,N-dimethylbenzylamine catalyst, the vial capped and the reaction mixture heated in an oven for 1 hour at 120° C. The amber, tacky, thermoplastic product,

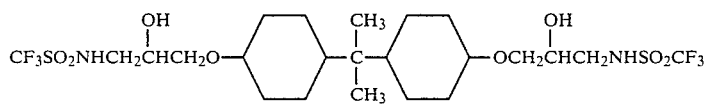

(A)

was heated with an additional 3.8 g of "Eponex 1510" epoxy resin to yield a hard, chain-extended, amber product. The 24 hour water absorption test resulted in a value of 0.17% percent by weight, a low value.

EXAMPLE XXI

Into a 100 mL flask equipped as described in Example XVI were placed 13.25 g (0.025 mole) of N-ethylperfluorooctanesulfonamide, 5.7 g (0.015 mole) of "Epon 828" epoxy resin, 0.1 g of triethylamine and 6.3 g of methyl isobutyl ketone solvent. The reaction mixture was stirred and heated for 15 hours at 100° C. GC and IR analysis of a small sample of the reaction mixture indicated the formation of the diol prepolymer

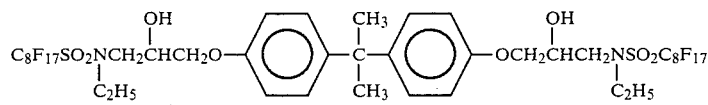

(B)

EXAMPLE XXII

This example describes the preparation of a urethane polymer from the fluorochemical diol prepolymer (B) of Example XXI.

To the solution containing the prepolymer diol (B) were added 14 g of methyl isobutyl ketone solvent, 3.28 g (0.0125 mole) of bis(4-isocyanatocyclohexyl)methane "Hylene W", and 0.1 g of dibutyltin dilaurate catalyst. The reaction mixture was heated for 3 hours at 85° C. to form a fluorochemical urethane polymer solution. A brittle film which was cast from this solution was found to have a surface energy of 14.6 dynes/cm$^2$, a low value.

EXAMPLE XXIII

This example describes the preparation of a flexible urethane polymer from the fluorochemical diol (B) of Example XXI. To the solution containing the fluorochemical diol, prepared as in Example XXI, was added 50.5 g of methyl isobutyl ketone solvent, 12.25 g (0.0125 mole) of "Rucoflex S1019-112" polyester diol, 6.55 g (0.025 mole) of "Hylene W" diisocyanate, and 0.1 g of dibutyltin dilaurate. The reaction mixture was heated for 3 hours at 85° C. to form a fluorochemical urethane/polyester polymer solution. A tough, flexible film which was cast from this solution was found to have a surface energy of 14.7 dynes/cm$^2$, a low value.

EXAMPLE XXIV

To a 100 mL flask equipped as described in Example XVI were added 3.75 g (0.025 mole) of "ERL-4206" epoxy resin, 13.25 g (0.025 mole) of N-ethylperfluorooctanesulfonamide, 6 g methyl isobutyl ketone solvent, and 0.034 g of sodium borohydride catalyst. The reaction mixture was stirred and heated for 12 hours at 120° C., diluted with an additional 6 g of methyl isobutyl ketone, and allowed to cool. A small amount of suspended solids was allowed to settle. The clear solution was decanted from the reaction flask and concentrated to yield the fluorochemical epoxy compound

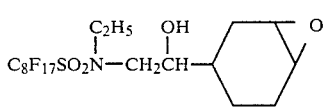

as indicated by IR and NMR spectral analysis.

Various modifications and alterations of this invention will become apparent to those skilled in the art without departing from the scope and spirit of this invention, and it should be understood that this invention is not to be unduly limited to the illustrative embodiments set forth herein.

What is claimed is:
1. A compound containing
   (A) a fluoroaliphaticsulfonamido moiety, and
   (B) a moiety containing
      (1) at least two oxirane groups,

(2) at least two non-terminal N-β-hydroxyalkylene groups, or
(3) at least one oxirane group and at least one non-terminal N-β-hydroxyalkylene group.

2. The compound of claim 1 having the following general formula:

$$R_fSO_2N(R^1)_2$$

wherein
$R_f$ represents a monovalent fluoroaliphatic radical,
$R^1$ represents a member selected from the group consisting of

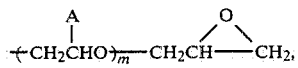

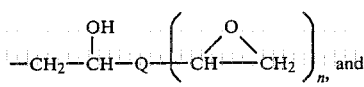 and

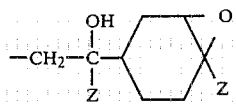

m is an integer equal to or greater than 0,
n is an integer equal to or greater than 1,
Q represents a linking group,
A represents hydrogen or hydrocarbon radical, and
Z represents hydrogen or methyl radical.

3. The compound of claim 1 having the following general formula:

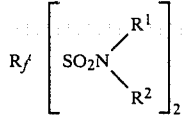

wherein
$R_f'$ represents a divalent fluoroaliphatic radical,
$R^1$ represents a member selected from the group consisting of

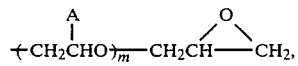

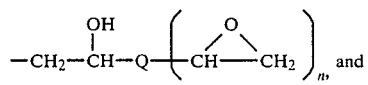 and

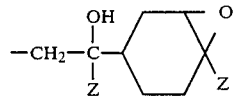

m is an integer equal to or greater than 0,
n is an integer equal to or greater than 1,
Q represents a linking group,
A represents hydrogen or hydrocarbon radical,
Z represents hydrogen or methyl radical, and
$R^2$ represents a member selected from the group consisting of hydrogen, unsubstituted hydrocarbon radical, substituted hydrocarbon radical, and $R^1$.

4. A compound having the formula:

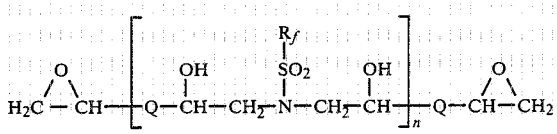

wherein
$R_f$ represents a divalent fluoroaliphatic radical,
Q represents a linking group, and
n is an integer equal to or greater than 1.

5. The compound of claim 1 having the following general formula:

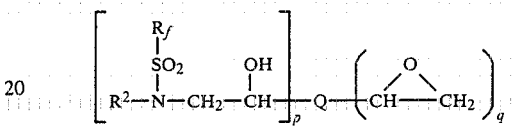

wherein
$R_f$ represents a divalent fluoroaliphatic radical,
Q represents a linking group,
p is an integer equal to or greater than 1,
q is an integer equal to or greater than 0,
p+q is equal to or greater than 2, and
$R^2$ represents a member selected from the group consisting of hydrogen, unsubstituted hydrocarbon radical, substituted hydrocarbon radical, and $R^1$.

6. A compound having the formula:

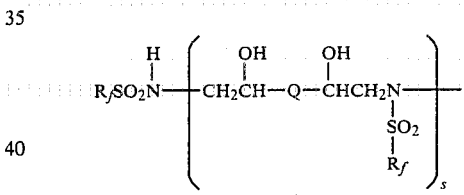

wherein
$R_f$ represents a divalent fluoroaliphatic radical,
Q represents a linking group, and
s is an integer equal to or greater than 1.

7. A compound having the formula:

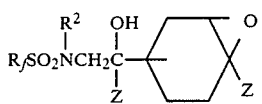

wherein
$R_f$ represents a divalent fluoroaliphatic radical,
$R^2$ represents a member selected from the group consisting of hydrogen, unsubstituted hydrocarbon radical, substituted hydrocarbon radical, and $R^1$.
Z represents hydrogen or methyl radical.

8. The compound of claim 1, said compound being selected from the group consisting of
N,N-Bis(2,3-epoxypropyl)perfluorooctanesulfonamide,
N,N-Bis(2,3-epoxypropyl)perfluorohexanesulfonamide,
N,N-Bis(2-glycidoxyethyl)perfluorooctanesulfonamide, and N,N'-Dimethyl-N,N'-bis(2,3-epoxypropyl)octafluorobutane-1,4-disulfonamide.

9. A compound selected from the group consisting of $$C_8F_{17}SO_2N \!\!\!\begin{array}{c}\end{array}\!\!\!(CH_2\overset{OH}{\underset{|}{C}}HCH_2OCH_2CH_2CH_2\overset{CH_3}{\underset{|}{\underset{CH_3}{Si}}}O-\overset{CH_3}{\underset{|}{\underset{CH_3}{Si}}}CH_2CH_2CH_2OCH_2\overset{O}{\overset{/\ \backslash}{CH-\!\!-\!\!CH_2}})_2$$

$$C_8F_{17}SO_2N \!\!\left(\!\!\!\begin{array}{c}\end{array}\!\!\!CH_2\overset{OH}{\underset{|}{C}}HCH_2O(CH_2\overset{CH_3}{\underset{|}{C}}HO)_{3.4}CH_2\overset{CH_3}{\underset{|}{C}}HOCH_2\overset{O}{\overset{/\ \backslash}{CH-\!\!-\!\!CH_2}}\!\!\right)_{\!\!2}$$

$$C_8F_{17}SO_2N(CH_2\overset{OH}{\underset{|}{C}}HCH_2N\!\!\!\underset{\underset{O}{\overset{\|}{C}}\!\!-\!\!\!\underset{\underset{C_2H_5}{|}}{\overset{|}{C}}\!\!-\!\!CH_3}{\overset{\overset{O}{\overset{\|}{C}}}{\diagdown}}NCH_2\overset{O}{\overset{/\ \backslash}{CH-\!\!-\!\!CH_2}})_2$$

$$C_8F_{17}SO_2N\!\!\!\begin{array}{c}\end{array}\!\!\!(CH_2\overset{OH}{\underset{|}{C}}HCH_2O\!\!-\!\!\!\bigcirc\!\!-\!\!\overset{CH_3}{\underset{\underset{CH_3}{|}}{\overset{|}{C}}}\!\!-\!\!\!\bigcirc\!\!-\!\!OCH_2\overset{O}{\overset{/\ \backslash}{CH-\!\!-\!\!CH_2}})_2$$

$$\overset{O}{\overset{/\ \backslash}{CH_2-\!\!-CH}}CH_2O-Q'-O(CH_2\overset{OH}{\underset{|}{C}}HCH_2\underset{\underset{SO_2C_8F_{17}}{|}}{N}CH_2\overset{OH}{\underset{|}{C}}HCH_2O-Q'-O)_2CH_2\overset{O}{\overset{/\ \backslash}{CH-\!\!-CH_2}}$$

where Q' is $-\!\!\bigcirc\!\!-\!\!\overset{CH_3}{\underset{\underset{CH_3}{|}}{\overset{|}{C}}}\!\!-\!\!\bigcirc\!\!-$ $$CF_3SO_2NHCH_2\overset{OH}{\underset{|}{C}}HCH_2O\!\!-\!\!\!\bigcirc\!\!-\!\!\overset{CH_3}{\underset{\underset{CH_3}{|}}{\overset{|}{C}}}\!\!-\!\!\!\bigcirc\!\!-\!\!OCH_2\overset{OH}{\underset{|}{C}}HCH_2NHSO_2CF_3$$

$$C_8F_{17}SO_2\underset{\underset{C_2H_5}{|}}{N}CH_2\overset{OH}{\underset{|}{C}}HCH_2O\!\!-\!\!\!\bigcirc\!\!-\!\!\overset{CH_3}{\underset{\underset{CH_3}{|}}{\overset{|}{C}}}\!\!-\!\!\!\bigcirc\!\!-\!\!OCH_2\overset{OH}{\underset{|}{C}}HCH_2\underset{\underset{C_2H_5}{|}}{N}SO_2C_8F_{17}$$

$$C_8F_{17}SO_2\underset{\underset{CH_2CH}{\overset{C_2H_5}{|}}}{N}\!\!-\!\!CH_2\overset{OH}{\underset{|}{C}H}\!\!-\!\!\bigcirc\!\!\!\overset{O}{\diagup}$$

10. Method of preparing the compound of claim 1 comprising reacting a fluoraliphaticsulfonamide with a compound selected from the group consisting of epoxy-containing materials having more than one oxirane ring and epoxy-containing materials having a single oxirane ring vicinal to a group capable of being displaced.

11. The method of claim 10 wherein the epoxy-containing material is epichlorohydrin.

12. The method of claim 10 wherein the reaction is conducted in the presence of a catalyst.

13. The method of claim 10 wherein the reaction is conducted in the presence of a base.

14. A polymer prepared by curing a composition containing the compound of claim 1.

15. A composition which comprises
   (a) the compound of claim 1, and
   (b) a curing agent.

16. Method of curing a composition containing the compound of claim 1 comprising the steps of
   (1) mixing said compound with a curing agent, and
   (2) heating the mixture formed in step (1).

17. The method of claim 16, wherein said curing agent is selected from the group consisting of polyamines, anhydrides, polycarboxylic acids, and diisocyanates.

* * * * *

UNITED STATES PATENT AND TRADEMARK OFFICE
CERTIFICATE OF CORRECTION

PATENT NO. : 4,533,713

DATED : August 6, 1985

INVENTOR(S) : Richard D. Howells

It is certified that error appears in the above-identified patent and that said Letters Patent is hereby corrected as shown below:

Information missing: Attorney, Agent, or Firm - Donald M. Sell; James A. Smith; David L. Weinstein Col. 1, line 24 "eepoxy" should read --epoxy--.

Col. 4, line 18 "straightt" should read --straight--.

Col. 4, line 63 "$A_f$" should read --$R_f$--.

Col. 13, line 16 "perfluoctanesulfonamide" should read --perfluorooctanesulfonamide--.

Col. 17, line 21 "bis(b 3-glycidoxypropyl)" should read --bis(3-glycidoxypropyl)--.

Col. 17, line 21 "and (b" should read --and--.

Col. 17, line 34 "Ir" should read --IR--.

Col. 20, line 45 "(0.78)" should read --(0.87)--.

Signed and Sealed this

Nineteenth Day of November 1985

[SEAL]

Attest:

DONALD J. QUIGG

Attesting Officer

Commissioner of Patents and Trademarks